(12) United States Patent
Biedermann et al.

(10) Patent No.: US 7,276,069 B2
(45) Date of Patent: Oct. 2, 2007

(54) CONNECTOR ELEMENT FOR BONE RODS OR SPINAL RODS

(75) Inventors: Lutz Biedermann, VS-Villingen (DE); Jürgen Harms, Karlsruhe (DE); Peter Ostermann, Bocholt (DE)

(73) Assignee: Biedermann Motech GmbH, Schwenningen (DE)

( * ) Notice: Subject to any disclaimer, the term of this patent is extended or adjusted under 35 U.S.C. 154(b) by 442 days.

(21) Appl. No.: 10/221,840

(22) PCT Filed: Jan. 4, 2002

(86) PCT No.: PCT/EP02/00042

§ 371 (c)(1),
(2), (4) Date: Sep. 12, 2002

(87) PCT Pub. No.: WO02/054965

PCT Pub. Date: Jul. 18, 2002

(65) Prior Publication Data

US 2003/0114852 A1    Jun. 19, 2003

(30) Foreign Application Priority Data

Jan. 12, 2001 (DE) ............................. 101 01 478

(51) Int. Cl.
A61F 2/30 (2006.01)
(52) U.S. Cl. ............................. 606/61; 606/59; 606/72
(58) Field of Classification Search ................. 606/59, 606/54, 64, 87, 72; 423/124, 156, 165, 186, 423/202, 287, 295
See application file for complete search history.

(56) References Cited

U.S. PATENT DOCUMENTS

| 5,092,867 | A |   | 3/1992  | Harms et al. |
|-----------|---|---|---------|--------------|
| 5,154,719 | A | * | 10/1992 | Cotrel ........................ 606/73 |
| 5,261,907 | A |   | 11/1993 | Vignaud et al. |
| 5,397,363 | A | * | 3/1995  | Gelbard ...................... 606/61 |
| 5,672,176 | A |   | 9/1997  | Biedermann et al. |
| 5,702,393 | A | * | 12/1997 | Pfaifer ....................... 606/61 |
| 5,980,523 | A |   | 11/1999 | Jackson ...................... 606/61 |
| 6,030,386 | A | * | 2/2000  | Taylor et al. ................ 606/56 |
| 6,171,311 | B1| * | 1/2001  | Richelsoph .................. 606/61 |
| 2002/0169448 | A1 |  | 11/2002 | Vanacker |

FOREIGN PATENT DOCUMENTS

| DE | 38 23 737 C2 | 1/1990 |
| DE | 692 06 318 T2 | 11/1992 |
| EP | 0 514 303 A1 | 11/1992 |
| EP | 0 732 081 A1 | 9/1996 |
| FR | 2 795 622 | 1/2001 |
| WO | WO91/16020 | 10/1991 |
| WO | WO 00/59387 | 10/2000 |

* cited by examiner

*Primary Examiner*—Bruce Snow
(74) *Attorney, Agent, or Firm*—Christie, Parker & Hale, LLP

(57) ABSTRACT

A connecting element for connecting two rods or screws used for bone or vertebra stabilization is provided. The connecting element comprises a connecting portion, a first portion which can be connected to one of the rods and a second portion which can be connected to the other rod. In order that not only rods parallel to each other, but also those inclined at an angle to each other or oblique can be fixed to each other, the first portion is connected to the connecting portion by a device allowing polyaxial orientation.

13 Claims, 2 Drawing Sheets

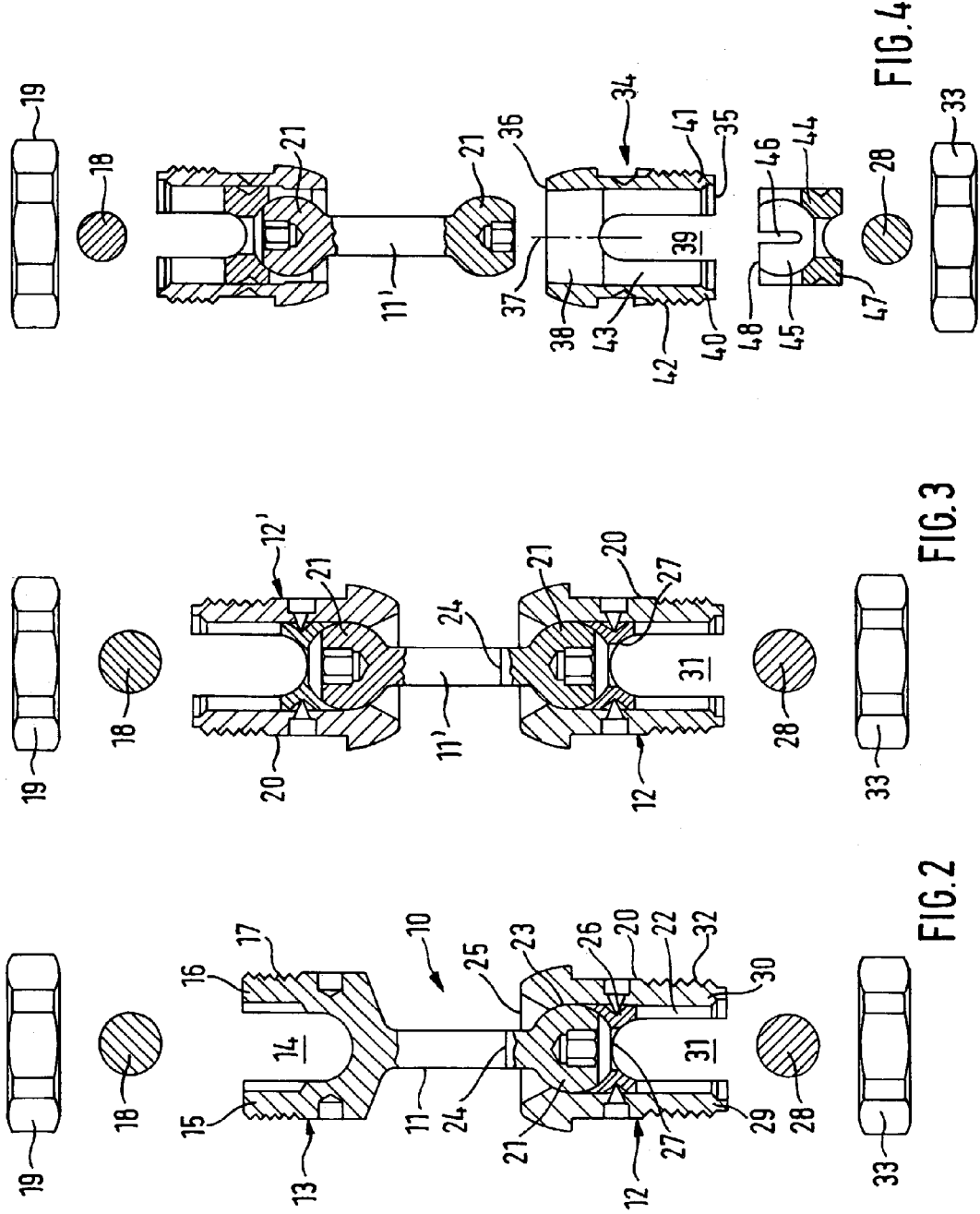

CONNECTOR ELEMENT FOR BONE RODS OR SPINAL RODS

CROSS-REFERENCE TO RELATED APPLICATION(S)

This patent application claims the benefit of priority of Germany Patent Application No. 101 01 478.3, filed Jan. 12, 2001.

BACKGROUND OF THE INVENTION

The invention concerns a connecting element for connecting two rod-like elements used for bone or vertebra stabilization.

A connecting element of this kind is known from DE 692 06 318 T2. The connecting portion is formed from two rods which are to be connected to each other at one end and which at the elements to be connected are gripped by sockets which are designed to be pivotable about a common screw extending transversely to the rod direction. The ends of the connecting portion comprise rings which can be fitted on screws which can be connected to the rods to be connected. From WO 91/16020 is known a connecting portion comprising two cylinder section-shaped channels which serve to receive two rods parallel to each other. Connection of rods inclined at an angle to each other or extending obliquely to each other is therefore not possible.

SUMMARY OF THE INVENTION

It is the object of the invention to provide a connecting element of the kind described hereinbefore, which allows connection of rods inclined at an angle to each other or extending obliquely to each other.

This object is achieved by the connecting element described hereafter. A connecting element of this kind has the great advantage that the surgeon is free to orient the rods according to the desired orientation of the parts to be connected.

BRIEF DESCRIPTION OF THE DRAWINGS

Further characteristics and advantages of the invention are apparent from the description of practical examples with reference to the figures. The figures show:

FIG. 2 a sectional view through a first embodiment of a connecting element; and

FIG. 3 a sectional view through a second embodiment of a connecting element; and FIG. 4 a sectional view through a modified embodiment.

DETAILED DESCRIPTION OF THE INVENTION

Figure 1:
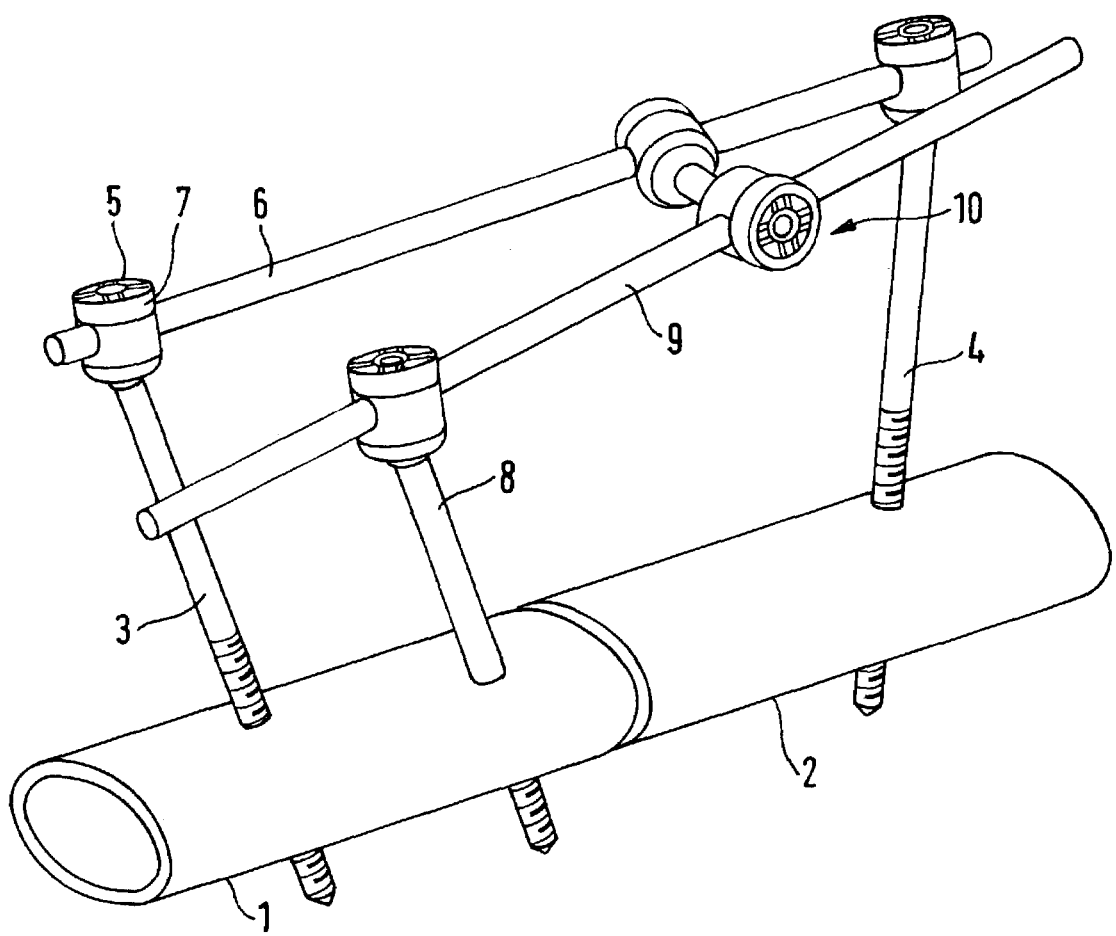
FIG. 1 a perspective view of an application.

In FIG. 1 are shown two long bone portions 1 and 2 to be connected to each other and fixed relative to each other. Into each of the two portions is screwed a screw 3, 4 known from vertebral column surgery as a pedicle screw. Each of the screws comprises a head 5 with a receiving opening for receiving a rod 6. By means of a nut 7, the rod is rigidly connected to the head. As can be seen from FIG. 1, into the portion 1 is screwed a third screw 8 which is designed exactly like the first two screws and receives a second rod 9 in its head.

The second rod 9 is connected to the first rod 6 by a connecting element 10. As a result, additional stabilization is set up.

In the above practical example, the two portions 1 and 2 to be connected are long bone portions. In the same way, at least two rods with corresponding screws are used to receive same in vertebral column surgery, for example internally in the case of a fixator, as known from DE 38 23 737-C, for instance.

The connecting element 10 comprises, in the embodiment shown in FIG. 2, a shank 11 with a first portion 12 at one end and a second portion 13 at its other end.

The second portion 13 includes two arms 15, 16 defining a U-shaped channel 14. The two arms 15, 16 have a cylindrical shape on the outside and have an external thread 17 at their free ends. The U-shaped channel 14 has a diameter which is essentially equal to or slightly larger than the diameter of a rod 18 to be received and which is made so large that the rod 18 can be introduced into the U-shaped channel 14 and guided by the latter in a lateral direction. Also provided is a nut 19 which is provided with its internal thread in such a way that it cooperates with the external thread 17. The thread 17 is designed in such a way that the distance from the thread to the bottom of the U-shaped channel 14 is smaller than the diameter of the rod 18, so that the rod 18 laid in the U-shaped channel 14 can be fixed by screwing on the nut 19.

As can be seen from FIG. 2, the other end of the second portion 13 comprises a head 21 having a spherical section. The first portion 12 comprises a cylindrically shaped socket 20 whose diameter is essentially equal to or slightly larger than the diameter of the head 21 and dimensioned such that the head can be introduced into the bore 22 and guided by the latter.

In the practical example shown, the bore 22 comprises a bottom 23 which is spherically shaped, its radius being equal to the radius of the head 21. As can be seen from FIGS. 2 and 3, the shank 11 is designed so that it can be separated from the spherical head by a screw joint.

In one embodiment, the connecting element 10 is designed in such a way that separation from the first and second portions is possible. In the practical example shown in FIGS. 2 and 3, separation is effected at the location of the shank 11 or 11' marked 24. For this purpose one shank portion comprises a threaded bore, while the other shank portion comprises a threaded attachment which can be screwed into the threaded bore. This connection is shown schematically by the connecting point 24. The threaded bore can also be provided directly in the head 21, and the shank 11 then has, at its end facing towards the head, a correspondingly shaped screw attachment which can be brought into engagement with the threaded bore for screwing the two portions together.

In the embodiment shown in FIG. 2, first the shank 11 is unscrewed from the head 21, so that the head 21 can be introduced from the free end of the bore 22 into the latter in the position shown. Then the shank 11 is screwed on, so that the connection shown in the figure is made.

As FIG. 2 further reveals, adjoining the bottom 23 is a second bore 25 which widens outwards in a funnel shape, so that the shank 11 is pivotable through a dihedral angle relative to the socket 20.

After the head 21 is introduced, in the bore 22 is inserted a pressure element 26 which is shaped spherically on its side facing towards the head, with a radius which corresponds to the radius of the head 21. On its side facing away from the head 21, the pressure element comprises a cylindrical surface 27 at which the diameter of this cylinder is almost equal to the diameter of the rod 28 to be received, such that the rod 28 can be laid in the recess 27. As can be seen from FIG. 2, the recess is further designed in such a way that a U-shaped channel 31 coaxial with the bore 22 with arms 29, 30 defining the channel 31 is formed. The two arms 29, 30 comprise, like the second portion 13, adjoining their free ends an external thread 32 which extends so far towards the other end of the socket 20 that its distance from the bottom of the cylindrical recess is smaller than the diameter of the rod 28. Also provided is a nut 33 whose internal thread corresponds to the external thread 32.

In operation, in the connecting portion prepared as described above, first the rod 18 is inserted in the monoaxially acting second portion 13 or in its U-shaped channel 14. Then the rod 18 is fixed by means of the nut 19. Next the socket 20 is oriented so as to receive the second rod 28 in it. After introducing the intermediate rod 28, the nut 33 is screwed on. The latter not only fixes the rod 28, but also exerts such pressure on the head 21 via the rod 28 and the pressure element 26 that the head 21 is fixed in its axial position.

In the embodiment shown in FIG. 3, the socket 20, the pressure element 26, the head 21, the rod 28 and the nut 33 correspond in all details to the first portion 12 in FIG. 2. The embodiment differs only in that the second portion is designed not as a monoaxial connection, but likewise as a polyaxial connection. This second portion 12' is inversely symmetrical to the first portion 12. All parts of socket, head, pressure element, rod and nut match the corresponding parts of the first portion 12. For assembly the shank 11' is, as in the practical example described above, releasable by a screw joint along the line 24. After insertion of the head 21, the two portions of the shank 11' are rigidly connected to each other.

In operation, the connection is made as described above with reference to the first portion 12, wherein, before fixing, each of the sockets 20 is oriented in each case towards the rod 18, 28 to be received and then the rod is laid in and fixed by the nut 19, 33. By exerting the pressure from the nut via the rod 18, 28 and the pressure element, the head too is then finally fixed in its position.

In a modified embodiment, not shown, the socket 20 or the second portion 13 can in each case adjoining its free end comprise another internal thread into which an inner screw can be screwed in order thus to achieve locking of the screw joint in a manner known in the art.

In the embodiments described above, the head 21 is in each case inserted from the free end of the U-shaped recess. In a modified embodiment, the bore 22 can extend through the whole of the socket. The head is then inserted from the end of the bore 22 facing away from the arms, and held in the bore with a locking ring or snap ring to be fitted. It is crucial that the free edge which surrounds the head at the end facing towards the shank 11 widens outwards conically, in order to allow polyaxial movement between socket and head or shank.

The embodiment shown in FIG. 4 fully matches the embodiment described in FIG. 3 with respect to shank 11', head 21, rod 18 or 28 and nut 19 or 33. The socket 34 is designed differently. This socket 34 comprises a first end 35 and a second end 36 opposite the latter. A bore 38 coaxial with the axis of symmetry 37 of the socket is provided. Also there is a U-shaped recess 39 which starts from the first end 35 and which extends transversely to the axis of symmetry 39. The U-shaped recess is defined by two arms 40, 41. Adjoining the first end 35, the two arms 40, 41 comprise an external thread 42. The diameter of the U-shaped recess 39 is equal to or slightly larger than the diameter of the rod 18 or 28, and so large that the rod can be introduced into the recess and is laterally guided by the sides of the U-shaped recess. The external thread 42 is, as in the embodiments described above, formed so far to the bottom of the U-shaped recess that the distance from the U-shaped bottom is smaller than the diameter of the rod to be received. Further, as in the practical example described above, there is provided a nut 33 which cooperates with the external thread 42.

Unlike the practical examples described above, the cylindrical section 43 of the coaxial bore extends as far as a preset distance from the second end 36, and from there to the second end 36 tapers conically with a cone angle. Also provided is a pressure element 44 whose outer surface is conically shaped towards the second end 36 in a region 45 laterally encompassing the head 21, the cone angle corresponding to that of the conical region of the bore. The conical region comprises a slot 46 directed towards the second end 36 and opening towards this end. Due to adaptation of the cone surfaces between bore 38 and pressure element 44, self-locking occurs in the fully inserted state. The pressure element comprises, in the manner known from EP 0 732 081, a first end 47 and a second end 48 opposite the latter. Adjoining the first end there is provided an essentially cylindrical section whose outside diameter is selected so that the pressure element can slide in the cylindrical section 43. As can be seen from the figure, the pressure element comprises in its second region a spherical segment-shaped recess 45 opening towards the second end 48 for receiving the screw head. In other respects the socket 34 and the pressure element 44 match the disclosure in the above-mentioned EP 0 732 081, which is hereby made part of the description.

The device shown in FIG. 4 is constructed inversely symmetrically, so that the other end of the shank 11' is designed with its head, the socket and the pressure element identical with the one described above.

In operation, the pressure element is inserted in the socket 34 from the first end 35. From the second end 36, the head 21 is inserted or pressed into the region 45. Then the rod 28 is laid in the remaining U-shaped slot, and by screwing on the outer nut 33 pressure is exerted on the rod 28 and via the latter on the pressure element 44 encompassing the head 21 in such a way that rod 28 and ball head 21 are fixed in position. The procedure is the same on the opposite side.

This version too allows pivoting of the shank 11' through a preset dihedral angle and about the axis of symmetry 37, so that orientation or adaptation to the rods to be connected or rods with bolts is possible.

Alternatively, the device can also be designed in such a way that a head with socket is designed in the fashion shown in FIG. 4 and the other head is shaped in the monoaxial fashion described in FIG. 2.

In the practical examples described above, the connecting elements are always described for the connection of rods. In the same way two shanks of two screws or one shank of one screw and one rod can also be connected with the connecting element and fixed.

The invention claimed is:

1. A connecting element for connecting two rod-like elements capable of use for bone or vertebra stabilization, the connecting element comprising:
   a rod-shaped connecting portion having a first end and an opposing second end, each of the first and second ends having an end piece attached thereto for engaging one of the two rod-like elements, at least a first end piece being structured and arranged to allow polyaxial orientation between a rod-like element engaged thereby and the connecting portion, wherein each piece has two arms that are threaded, the two arms having free ends and defining a U-shaped channel to receive a rod-like element, and a nut or screw interacting with the threaded arms for fixing the rod-like element in the channel;

wherein the first end and the second end of the rod-shaped connecting portion extend from the end pieces, respectively, at an end opposite to the free ends of the arms.

2. The connecting element according to claim 1, wherein the connecting portion comprises a head at the first end and the first end piece comprises a first receiving portion having a receiving opening defining the U-shaped channel for receiving the rod-like element, and a second receiving portion structured and arranged to receive the head to allow polyaxial orientation between the rod-like element engaged thereby and the connecting portion.

3. The connecting element according to claim 1, wherein a second end piece is monoaxially connected to the connecting portion.

4. The connecting element according to claim 3, wherein the connecting portion comprises a head at the first end and the first end piece comprises a first receiving portion having a receiving opening defining the U-shaped channel for receiving the rod-like element, and a second receiving portion structured and arranged to receive the head to allow polyaxial orientation between the rod-like element engaged thereby and the connecting portion.

5. The connecting element according to claim 1, wherein a second end piece is structured and arranged to allow polyaxial orientation between a rod-like element engaged thereby and the connecting portion.

6. The connecting element according to claim 5, wherein the connecting portion comprises a head at the first end and the first end piece comprises a first receiving portion having a receiving opening defining the U-shaped channel for receiving the rod-like element, and a second receiving portion structured and arranged to receive the head to allow polyaxial orientation between the rod-like element engaged thereby and the connecting portion.

7. The connecting element according to claim 6, wherein the connecting portion comprises a head at the second end and the second end piece comprises a first receiving portion having a receiving opening defining the U-shaped channel for receiving the rod-like element and a second receiving portion structured and arranged to receive the head at the second end to allow polyaxial orientation between the rod-like element engaged thereby and the connecting portion.

8. The connecting element according to claim 2, wherein the head includes a spherical section and the second receiving portion includes a corresponding spherical portion to allow the polyaxial orientation.

9. The connecting element according to claim 4, wherein the head includes a spherical section and the second receiving portion includes a corresponding spherical portion to allow the polyaxial orientation.

10. The connecting element according to claim 7, wherein the head at the first end includes a spherical section and the second receiving portion of the first end piece includes a corresponding spherical portion to allow the polyaxial orientation; and wherein the head at the second end includes a spherical section and the second receiving portion of the second end piece includes a corresponding spherical portion to allow the polyaxial orientation.

11. A connecting element for connecting two rod-like elements capable of use for bone or vertebra stabilization, the connecting element comprising:

a rod-shaped connecting portion having a first end and an opposing second end, each of the first and second ends having an end piece attached thereto for engaging one of the two rod-like elements, at least a first end piece being structured and arranged to allow polyaxial orientation between a rod-like element engaged thereby and the connecting portion, wherein each end piece has two arms defining a U-shaped channel to receive a rod-like element, a thread provided on the arms at free ends of the arms, and a nut or screw interacting with the thread for fixing the rod-like element in the channel;

wherein the first end and the second end of the rod-shaped connecting portion extend from the end pieces, respectively, at an end opposite to the free ends of the arms.

12. The connecting element according to claim 11, wherein the connecting portion comprises a head at the first end and the first end piece comprises a first receiving portion having a receiving opening defining the U-shaped channel for receiving the rod-like element, and a second receiving portion structured and arranged to receive the head to allow polyaxial orientation between the rod-like element engaged thereby and the connecting portion.

13. The connecting element according to claim 12, wherein the head includes a spherical section and the second receiving portion includes a corresponding spherical portion to allow the polyaxial orientation.

* * * * *

UNITED STATES PATENT AND TRADEMARK OFFICE
CERTIFICATE OF CORRECTION

PATENT NO. : 7,276,069 B2  Page 1 of 1
APPLICATION NO. : 10/221840
DATED : October 2, 2007
INVENTOR(S) : Lutz Biedermann et al.

It is certified that error appears in the above-identified patent and that said Letters Patent is hereby corrected as shown below:

In the Claims

Column 5, line 4, claim 1         Insert --end-- after "each"

Signed and Sealed this

Eighth Day of April, 2008

JON W. DUDAS
*Director of the United States Patent and Trademark Office*